United States Patent [19]

Kira

[11] Patent Number: 4,921,495

[45] Date of Patent: * May 1, 1990

[54] POROUS ARTIFICIAL VESSEL

[75] Inventor: Kazuaki Kira, Kobe, Japan

[73] Assignee: Kanegafachi Kagaku Kogyo Kabushiki Kaisha, Japan

[*] Notice: The portion of the term of this patent subsequent to Feb. 16, 2005 has been disclaimed.

[21] Appl. No.: 842,956

[22] Filed: Mar. 24, 1986

Related U.S. Application Data

[63] Continuation-in-part of Ser. No. 617,401, Jun. 5, 1984, abandoned.

[30] Foreign Application Priority Data

| Jun. 6, 1983 | [JP] | Japan | 58-101520 |
| Feb. 29, 1984 | [JP] | Japan | 59-39077 |
| Mar. 1, 1984 | [JP] | Japan | 59-39971 |
| Mar. 7, 1984 | [JP] | Japan | 59-44396 |
| Mar. 7, 1984 | [JP] | Japan | 59-44397 |

[51] Int. Cl.$^5$ .................................. A61F 2/00
[52] U.S. Cl. ........................... 623/1; 623/66; 606/153
[58] Field of Search ............ 623/1, 66; 128/334 R; 264/DIG. 14, 45.5, 45.8, 46.9, 48; 425/817 C

[56] References Cited

U.S. PATENT DOCUMENTS

| 3,745,203 | 7/1973 | Harper | 264/48 |
| 3,991,147 | 11/1976 | Knipp et al. | 264/54 |
| 4,173,689 | 11/1979 | Lyman | 623/1 |
| 4,208,745 | 6/1980 | Okita | 623/1 |
| 4,234,535 | 11/1980 | Okita | 264/519 |
| 4,254,180 | 3/1981 | Kline | 428/323 |
| 4,286,341 | 9/1981 | Greer et al. | |
| 4,304,010 | 12/1981 | Mano | 623/1 |
| 4,321,711 | 3/1982 | Mano | 623/1 |
| 4,355,426 | 10/1982 | MacGregor | 128/334 R |
| 4,550,447 | 11/1985 | Seiler, Jr. et al. | 623/1 |
| 4,604,762 | 8/1986 | Robinson | 128/334 R X |
| 4,623,347 | 11/1986 | Kira | 128/334 R X |
| 4,655,771 | 4/1987 | Wallsten | 623/1 |

FOREIGN PATENT DOCUMENTS

| 0002931 | 7/1979 | European Pat. Off. | 623/1 |
| 0130401 | 1/1985 | European Pat. Off. | |
| 1265246 | 3/1972 | United Kingdom . | |
| 2033233 | 5/1980 | United Kingdom . | |
| 2077107 | 12/1981 | United Kingdom . | |
| 2092894 | 8/1982 | United Kingdom . | |

OTHER PUBLICATIONS

Szycher et al., "Synthetic Biomedical Polymers Concepts and Applications", 1980, pp. 29-38.

Primary Examiner—Richard J. Apley
Assistant Examiner—Paul Prebilic

[57] ABSTRACT

An artificial vessel prepared from a solution of a thermoplastic elastomer in a good solvent, comprising a skin layer on at least the inner surface of the vessel wall, and an interior region having a spongy structure characterized by cells surrounded by partition walls, wherein the inner surface, outer surface, and partition walls contain:
(a) small pores of less than 1 μm in diameter formed by replacement of the good solvent in the solution of the elastomer with a coagulating liquid for the elastomer;
(b) large pores of 1 to 50 μm in diameter which are in continuous communication with each other and communicate the inner surface of the vessel wall to the outer surface of the vessel wall, the large pores being formed by elution of pore-forming particles contained in the solution of thermoplastic elastomer,
and wherein the porosity of the artificial vessel is 75 to 87.5% by volume, and the compliance of the artificial vessel is 0.1 to 0.8.

6 Claims, 1 Drawing Sheet

U.S. Patent May 1, 1990 4,921,495
FIG. 1
FIG. 2
FIG. 3
FIG. 4
FIG. 5
FIG. 6
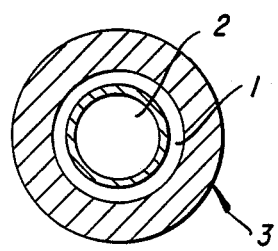
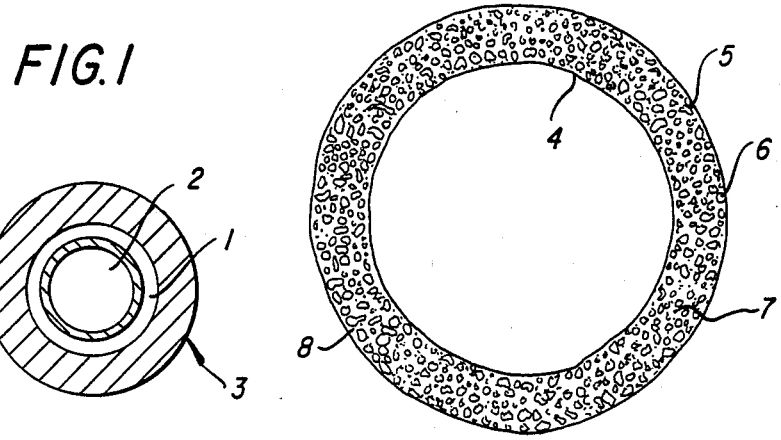
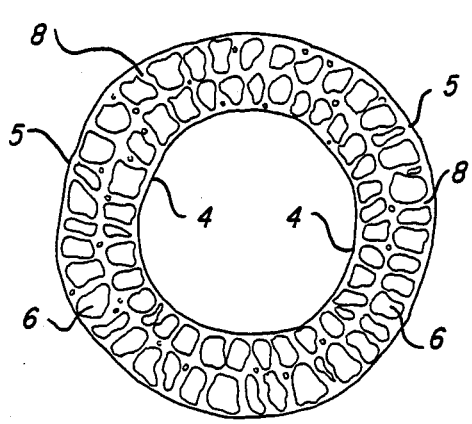
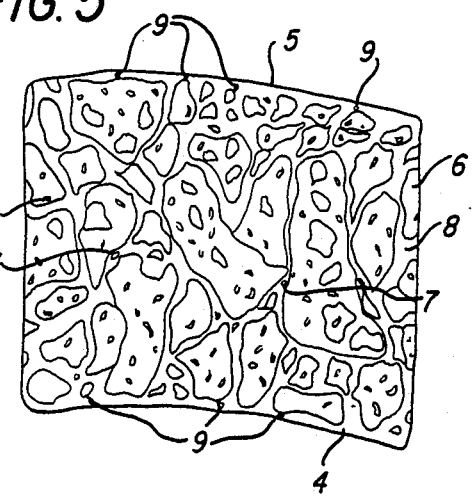
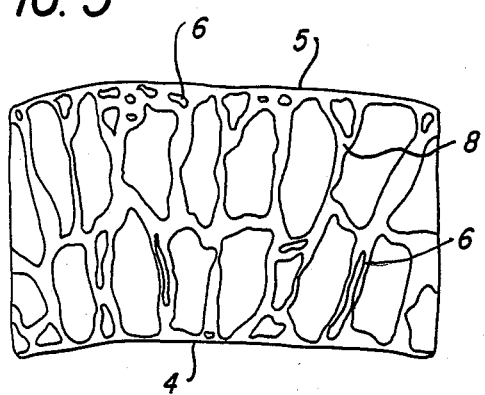
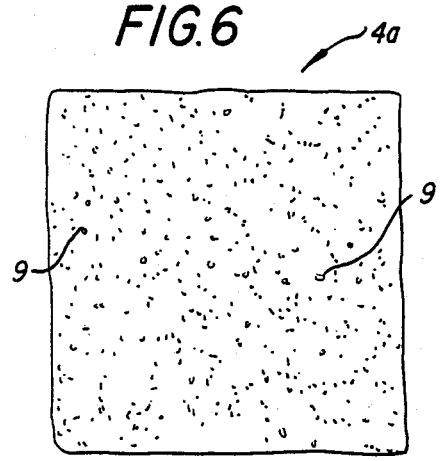

POROUS ARTIFICIAL VESSEL

CROSS-REFERENCE TO RELATED APPLICATION

This is a continuation-in-part of application Ser. No. 617,401 filed on June 5, 1984 and now abandoned.

BACKGROUND OF THE INVENTION

The present invention relates to an artificial vessel which has a compliance approximate to that of a vital vessel and a process for preparation of the same.

Many artificial vessels have been developed with the progress of vascular surgery. At present, examples of clinically used artificial arteries with a large diameter of not less than 6 mm are the DeBakey artificial vessel made of woven Dacron (USCI. Co., Ltd. of U.S.A.) and the Gore-Tex vessel (Gore. Co., Ltd. U.S.A.) which is made of expanded polytetrafluoroethylene (hereinafter referred to as "EPTFE")

In Sasajima et al, J. Artif. Organs, 12(1), 179–182 (1983), the compliances of the above artificial vessels were measured. The results are shown in Table 1.

TABLE 1

| Vessel | Compliance |
| --- | --- |
| Thoracic aorta of dog | 0.749 |
| Abdominal aorta of dog | 0.491 |
| Carotid artery of dog | 0.356 |
| Double Velour Dacron | 0.058 |
| Woven Dacron | 0.021 |
| EPTFE | 0.028 |

As shown in Table 1, the compliances of the conventional artificial vessels are much smaller than those of vital vessels, which causes various problems due to compliance mismatch, such as anastomotic punnus hyperplasia, a long time after the grafting of the vessel in a living body. Particularly, the conventional artificial vessels cannot be clinically used as an artificial artery with a small diameter of not more than 6 mm because the compliance mismatch remarkably increases at such a small diameter, causing poor patency of the vessel. Therefore, the patient's own veins are used for vascular reconstructive surgery of coronary arteries or arteries below the knees.

In order to solve such compliance mismatch, a process for preparing an artificial vessel from an elastomer which has a porous wall and a compliance approximate to that of a vital vessel is disclosed in U.S. Pat. No. 4,173,689 to Lyman. This artificial vessel is prepared by immersing a mandrel into an elastomer solution, taking the mandrel out of the solution, coating the mandrel with the solution, and immersing it into a poor solvent such as water to deposit the elastomer on the mandrel. However, this process can only provide a vessel having very small pores on its wall and having a relatively dense structure. Although the compliance of the artificial vessel prepared according to the process disclosed in the U.S. Pat. is larger than that of a conventional artificial vessel, its compliance is still smaller than that of a vital vessel and is not sufficient. In addition, since it is difficult to coat the mandrel uniformly with the elastomer solution, an artificial vessel having the same properties in all of its parts cannot be prepared.

An artificial vessel for arterial grafting which comprises at least two porous elastomer zones and a solid elastomer zone is disclosed in Japanese Unexamined Patent Publication (KOKAI) No. 150954/1982. As a result of the present inventor's study, it was found that an artificial vessel having the solid elastomer zone—porous elastomer zone—solid elastomer zone structure at its cross-section could not be prepared according to the procedures disclosed in the publication.

As mentioned above, in general the smaller the diameter of an artificial vessel for an artery becomes, the more it is important that the compliance of the vessel approximates that of a vital vessel. Although various efforts have been made to obtain an artificial vessel having a compliance approximate to that of a vital vessel, no artificial vessel having the required compliance has been realized.

Moreover, the preparations of the conventional artificial vessels are complicated, which makes the artificial vessels expensive.

In addition to compliance match, an artificial vessel requires properties such that the suture should not be readily frayed, the artificial vascular material can be optionally cut to a desired length, and no kinks are formed. When woven Dacron or woven polytetrafluoroethylene is used, a special textile technique is required in order for the vessel not to fray at the cut ends, and a special technique such as bellows processing is also required to avoid the formation of kinks, which makes the preparation of the vessel complicated and its price expensive. In the case of the EPTFE, a complicated preparation is required for stretching the PTFE, which makes the vessel expensive.

As a result of the inventor's continuous studies, it has been found that an inexpensive artificial vessel having a compliance approximate to that of a vital vessel can be prepared by extruding an elastomer solution from an annular nozzle and treating the inner and the outer sides of the tubular extrudate in a coagulating liquid. The artificial vessel obtained comprises a skin layer at least in the inner surface area of the vessel wall and a spongy structure in the inside region of the vessel wall.

SUMMARY OF THE INVENTION

According to the present invention there is provided an artificial vessel made of an elastomer, comprising a skin layer at least in the inner surface area of the vessel wall and a spongy structure in the inside region of the vessel wall, wherein the skin layer and the partition wall which forms the spongy structure have small pores of 1 to 50 μm in diameter and very small pores and/or holes of less than 1 μm in diameter, said artificial vessel having pores which communicate between the outside and the inside of the vessel wall, a porosity of 75 to 87.5% by volume and a compliance of 0.1 to 0.8. The artificial vessel can be prepared by extruding an elastomer solution together with an inside coagulating liquid from an annular nozzle, and immersing the tubular extrudate into an outside coagulating liquid.

BRIEF DESCRIPTION OF THE DRAWINGS

FIG. 1 shows a front view of the exit of the annular nozzle for the elastomer solution used in the present invention;

FIG. 2 shows a sketch of a photograph of a section of the artificial vessel prepared in Example 1 with a scanning type electron microscope;

FIG. 3 shows a magnified view of FIG. 2;

FIG. 4 shows a sketch of the photograph of a section of a artificial vessel prepared in Example 3 with a scanning type electron microscope;

FIG. 5 shows a magnified view of FIG. 4; and

FIG. 6 shows a sketch of a photograph of the inner surface of the artificial vessel prepared in Example 3 with a scanning type electron microscope.

DETAILED DESCRIPTION

The elastomer used in the present invention is a thermoplastic elastomer which has fine blood compatibility. Namely, the elastomer does not release any low molecular compound which causes acute poisoning, inflammation, hemolysis, fever, and the like, and does not subject the blood to serious damage. The thermoplastic elastomer also has a superior antithrombogenicity. Examples of the elastomers are polystyrene elastomers, polyurethane elastomers, polyolefin elastomers, polyester elastomers, elastomers which are blended with polymers to the extent where they retain the property of an elastomer, and a mixture thereof. From the viewpoints of strength, durability and antithrombogenicity, the polyurethane elastomers are more preferable. Examples of the polyurethane elastomers are, for instance, polyurethane, polyurethaneurea, and a mixture of those polymers with silicone polymers. From the viewpoint of durability in a living body, a polyether type is more preferable than a polyester type among the above-mentioned polyurethane and polyurethaneurea. A segmented polyurethane, a segmented polyurethaneurea, a segmented polyurethane or a segmented polyurethaneurea which contains fluorine atom in a hard segment or a soft segment, and a polyurethane or a polyurethaneurea as disclosed in Japanese Unexamined Patent Publication (KOKAI) No. 211358/1982, which contains dimethylsiloxane in its main chain are still more preferable. Particularly preferable elastomers are the polyurethane and the polyurethaneurea which contain dimethylsiloxane according to the formula:

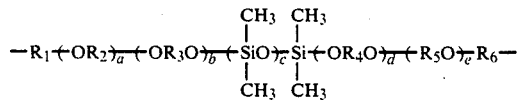

wherein each of $R_1$, $R_2$, $R_3$ $R_4$, $R_4$ and $R_5$ and $R_6$ is an alkylene group having at least 1 carbon atom, preferably an alkylene group having 2 to 6 carbon atoms such as ethylene, propylene, butylene or hexamethylene; a and e are 0 or an integer of 1 to 30; b and d are 0 or 1; c is an integer of not less than 2, and contain a polyether portion of the formula:

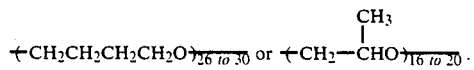

The artificial vessel of the present invention has a skin layer at least in the inner surface area and a spongy structure in the inside region. The skin layer is made of the elastomer and the structure of the skin layer is more uniform and dense than the structure of the inside region. The thickness of the skin layer varies depending on the strength of the elastomer used and the structure of the vessel wall. A preferable thickness of the skin layer is usually not more than 50 μm, more preferably 0.5 to 20 μm, most preferably 1 to 15 μm. When the thickness of the skin layer is more than 50 μm, the compliance of the artificial vessel tends to be too small. On the contrary, when the thickness of the skin layer is less than 0.5 μm, there is a danger that the artificial vessel may burst under the effect of blood pressure.

The skin layer in the present invention is not a layer having a transparent or clear appearance which is obtained from a dense structure of the elastomer molecules such as a cast film or a molded article made from a molten elastomer, but is a layer having a large number of very small pores and/or holes with the maximum diameter of less than 1 μm therein. These very small pores and/or holes are formed by replacement between a coagulating liquid and a good solvent for the elastomer when the elastomer solution is immersed into the coagulating liquid to precipitate the elastomer. Therefore, the skin layer in the present invention is more bulky than the above-mentioned film and molded article, and is opaque under observation with naked eyes.

Although the skin layer may not have communicating pores which communicate the inside of the vessel with the outside of the vessel, it is more preferable that the skin layer has communicating pores in order to form pseudointima and to stabilize the formed pseudointima.

The maximum diameter of the communicating pores on the skin layer surface is preferably 1 to 50 μm, more preferably 10 to 40 μm, most preferably 11 to 30 μm. When the maximum diameter is more than 50 μm, the strength of the artificial vessel tends to be small and leakage of blood in the first stage of grafting in a living body tends to be too large. When the maximum diameter is less than 1 μm, the communicating pores tend not to promote the formation of pseudointima and not to stabilize the formed pseudointima. In the absence of the communicating pores in the skin layer, however, holes with the maximum diameter of about 1 to 10 μm may exist in the skin layer.

The term "spongy structure" as used herein means a structure in which cells are aggregated. The cell is in the form of a sphere, an oval or a deformed variation thereof and has the maximum diameter of about 1 μm to about three-fifths the thickness of the vessel wall. The spongy structure region is more bulky than the skin layer. The partition wall which defines the cell in the spongy structure preferably contains a lot of very small pores and/or holes similar to the skin layer. A more preferable spongy structure is the double cell structure wherein two layers of cells are arranged between the inner skin layer and the outside of the vessel. The maximum diameter of the cell in the double cell structure is preferably about 1/5 to 3/5, more preferably about ⅓ to ½ the thickness of the vessel wall. Smaller cells than those cells may exist in a region where the cells are in contact with the skin layer. A particularly preferably spongy structure is a structure in which cells of uniform size are aggregated in the form of a sponge. In that case, the maximum diameter of the cell is preferably to 100 μm, more preferably 5 to 75 μm, most preferably 10 to 40 μm.

The partition wall which defines the cell and is made of the elastomer is not required to have communicating pores. However, it is preferable that the partition wall has communicating pores in order to give a porosity which is useful for the formation of pseudointima. The maximum diameter of the communicating pore is preferably about 1 to 50 μm, more preferably 10 to 40 μm, most preferably about 1 to 30 μm, which is the same as the diameter of the communicating pores on the skin layer surface. Further, partition walls which form the communicating pores themselves preferably have very small pores and/or holes with the maximum diameter of less than 1 μm and thus have a bulky structure, which improves the compliance and the patency of the vessel wall. These very small pores and/or holes are formed by replacement between a coagulating liquid and a good solvent for the elastomer when the elastomer solution is immersed into the coagulating liquid to precipitate the elastomer.

The "compliance" as used herein is defined by the equation (I):

$$C = \frac{\Delta V}{V_0 \cdot \Delta P} \times 100 \qquad (I)$$

wherein C is the compliance, Vo is the volume of a vessel measured at the inner pressure of 50 mmHg, $\Delta P$ is a pressure change of 100 mmHg in the inner pressure from 50 mmHg to 150 mmHg, $\Delta V$ is the increase in volume of the vessel when the inner pressure rises from 50 mmHg to 150 mmHg. In practical measurement, a vessel is inserted into a closed circuit, and the volume of an injected liquid and the pressure variation in the circuit are measured by means of a microanalysis pump and a pressure gauge. From the results, the compliance can be calculated according to the equation (I).

The artificial vessel of the present invention has a large compliance because the vessel is made of the elastomer and the density of the elastomer in the vessel wall is small. In addition, the compliance of the artificial vessel can be made approximate to that of a vital vessel by adjusting the density of the elastomer in the vessel wall, the porosity and the thickness of the vessel wall.

The preferable compliance for an artificial vessel cannot be absolutely defined because the compliance is different depending on the diameter of the vessel, the site to be grafted, and the like. In general, since the compliance of a vital vessel which is used for vascular reconstruction surgery is about 0.1 to 0.8, the compliance is preferably within the range mentioned above. According to the present invention, an artificial vessel with any compliance within the range of 0.1 to 0.8 can be produced. The artificial vessel with a compliance of 0.1 to 0.8 is preferably used as an artery. Particularly, the artificial vessel having an inside diameter of 1 to 6 mm with a compliance of 0.1 to 0.5 is preferably used as an artery having a small diameter.

The "compliance approximate to that of a vital vessel" means that the artificial vessel has a compliance approximate to that of a vital vessel having an inner diameter and a thickness of the vessel wall which are both approximate to those of the artificial vessel. Therefore, the artificial vessel having an inner diameter of from 2 to 6 mm, a thickness of the vessel wall of from 0.2 to 1.5 mm and a compliance of from 0.2 to 0.5 can preferably be used as arteries of a small diameter, and the artificial vessel having an inner diameter of from 2 to 6 mm, a thickness of the vessel wall of from 0.4 to 1.3 mm and a compliance of from 0.3 to 0.5 can more preferably be used as arteries of a small diameter.

The optimum density of the elastomer of the vessel wall varies depending on the porosity, the strength of the elastomer, the thickness of the vessel wall, the portion of the living body to be grafted. Thus, the density cannot be absolutely defined, but is preferably 0.05 to 0.35 g/cm$^3$, more preferably 0.1 to 0.3 g/cm$^3$, most preferably 0.125 to 0.25 g/cm$^3$ This value of 0.125 to 0.25 g/cm$^3$ for the density corresponds to a porosity of about 75 to 87.5% by volume, calculated from a specific gravity of about 1 for the typical elastomer. The range of from about 75 to 87.5% by volume for the porosity is preferable for improving the compliance and the patency.

The strength of the elastomer of the vessel wall varies depending on the density of the vessel wall, and the like. Thus the strength cannot be absolutely defined, but in general the tensile strength is preferably 100 to 700 kg/cm$^2$ and the elongation at break is preferably 100 to 1500 %. The thickness of the vessel wall may be matched with that of the vital vessel to be grafted.

The compliance of the artificial vessel of this invention can be made approximate to that of a vital vessel by adjusting the above-mentioned factors.

The inner surface area of the artificial vessel, that is, the surface area in contact with blood, is constituted by the skin layer of the elastomer having a superior blood compatibility. In order to improve the antithrombogenicity of the vessel in the first stage of grafting in a living body, the inside wall may be coated with albumin, gelatin, chondroitin sulfuric acid, a heparinized material, and the like. Also the outside wall of the artificial vessel may be reinforced with a net, a non-woven fabric, and the like, in order to impart resistance against an extraordinary increase in blood pressure during surgery or to maintain its durability for a long time.

The preparation of the artificial vessel of the present invention is explained in the following.

The artificial vessel of the present invention can be prepared by extruding the elastomer solution from an annular nozzle together with an inside coagulating liquid, and immersing the tubular extrudate into an outside coagulating liquid to precipitate the elastomer tubularly. In the extrusion step, the elastomer solution is fed into the annular nozzle and extruded tubularly. At the same time, the inside coagulating liquid is fed into the inside of the tubular extrudate of the elastomer solution at the rate of extrusion of the solution. The tubular extrudate of the elastomer solution is immersed immediately, or after passing through a dry space at a constant dry distance, into the outside coagulating liquid. The dry distance is preferably not more than 50 cm. It is particularly preferable that the elastomer solution extruded is immediately immersed into the outside coagulating liquid. When the dry distance is longer, the tubular extrudate tends to vary in size. The temperature of the elastomer solution, the temperatures of the inside and the outside coagulating liquids, the temperature of the annular nozzle and the temperature of the dry space are not particularly limited. Although the above-mentioned procedures are usually carried out at room temperature, when the viscosity of the elastomer solution is high, the temperature of the elastomer solution may be elevated to about 100° C. The elastomer extruded is immersed into the outside coagulating liquid and precipitated. After sufficiently removing the solvent and a pore-forming agent when the pore-forming agent is used, the tubular material obtained is cut to a desired length.

The above-mentioned annular nozzle can extrude the elastomer solution tubularly and can be charged with the inside coagulating liquid. An embodiment of the annular nozzle is explained in FIG. 1.

In FIG. 1 the annular nozzle 3 has an exit 1 for the elastomer solution. The inner diameter and the outer diameter of the exit 1 are selected according to the dimensions of the desired artificial vessel. The inside coagulating liquid is injected from an exit 2.

The elastomer solution in the present invention contains the above-mentioned elastomer and a good solvent which can dissolve the elastomer well. The elastomer solution may contain, as occasion demands, a pore-forming agent, a poor solvent which cannot dissolve the elastomer but is miscible with the good solvent, an inorganic salt, thiourea, and the like.

Examples of the good solvents are N,N-dimethylacetamide, N,N-dimethylformamide, dimethylsulfoxide, N-methyl-2-pyrrolidone, dioxane, tetrahydrofuran, a mixture thereof and the like. The good solvent should be selected according to the kind of elastomer used.

The above-mentioned pore-forming agent is used in order to prepare the communicating pores. The pore-forming agent is not particularly restricted as long as it is insoluble in the good solvent for the elastomer and can be removed during or after the preparation of the artificial vessel. Since the artificial vessel is grafted in a living body, it is desired that the pore-forming agent is pharmacologically acceptable. Examples of the pore-forming agents are an inorganic salt such as common salt, a water soluble saccharose such as glucose or starch, a protein, and the like. From the viewpoint of treatment, the protein is preferable, because even when the protein is finely divided, the fine particles do not form a secondary agglomeration due to moisture in the air, and thus can stably produce the pores. In addition, since the protein can be easily dissolved in an alkali solution, an acid solution and a solution of an enzyme, the removal of the protein can be easily carried out. Examples of the proteins are casein, collagen, gelatin, albumin, and the like. The particle size of the pore-forming agent is selected mainly depending on the maximum diameter of the pores to be formed in the inner surface area of the artificial vessel. The amount of the pore-forming agent (percentage of weight of the pore-forming agent to weight of the elastomer in the elastomer solution) varies depending on the required porosity and the particle size of the pore-forming agent. The preferable amount is 1 to 250%, more preferably 20 to 200%, most preferably 50 to 150%. When the amount of the pore-forming agent is more than 250%, the compliance is too large, the durability upon exposure to blood pressure is lowered, and the procedures for preparation become difficult because of the high viscosity of the elastomer solution. On the other hand, when the amount is less than 1%, the required porosity may not be obtained.

The poor solvent and the inorganic salt are used in order to control the structure of the vessel wall of the artificial vessel and the inside and the outside shapes of the vessel. Examples of the poor solvents are water, a lower alcohol, ethylene glycol, propylene glycol, 1,4-butane diol, glycerine, and the like.

The concentration of the elastomer in the elastomer solution is preferably 5 to 35% (% means % by weight hereinafter), more preferably 10 to 30%, most preferably 12.5 to 25%. When the concentration is less than 5%, the compliance tends to be too large and the precipitated elastomer in the coagulating liquid tends not to form a tube. On the other hand, when the concentration is more than 35%, the compliance tends to be too small and the elastomer solution is hard to extrude tubularly from the annular nozzle because of the high viscosity of the solution.

As the coagulating liquid, a poor solvent for the elastomer which does not dissolve the elastomer, but is miscible with the good solvent for the elastomer can be employed. Examples of the coagulating liquids are water, a lower alcohol, ethylene glycol, propylene glycol, 1,4-butane diol, glycerin, a mixture thereof and the like. The inside coagulating liquid and the outside coagulating liquid may be the same or different.

The structure of the artificial vessel of the present invention is explained below with reference to FIGS. 2 to 6 which show sketches of microscopic photographs of the artificial vessels prepared in the Examples explained hereinafter.

As shown in FIGS. 2 to 5 which show sketches of cross-sections of the artificial vessels, the skin layers 4, 5 exist in the inner surface area and in the outer surface area of the vessel wall. The cells 6 which are defined by the partition wall 8 exist between the skin layers 4 and 5. As shown in Fig. 2 and FIG. 3, the cells 6 are arranged in a double cell structure. In the artificial vessel shown in FIG. 4 and Fig. 5, the skin layers 4, 5 have many pores 9 (not shown in FIG. 4) which open to the outside, and the partition wall 8 has many pores 7 and some pores which communicate between the skin layers 4 and 5. The communicating pores which reach the surface of the skin layer form the openings of the pores 9 (shown in FIG. 6) on the inner surface 4a.

As mentioned above, according to the process of the present invention, an artificial vessel having a compliance which agrees with that of a vital vessel can be prepared, even when the inner diameter and the thickness of the artificial vessel match those of a vital vessel.

Since the artificial vessel of the present invention is substantially constructed by a sequence of the elastomer, the cut ends of the vessel are not frayed even if the vessel is cut to any length. Further, the vessel wall is bulky as a whole, and also the partition wall has fine pores which are formed by precipitation of the elastomer by substitution of the good solvent with the poor solvent. Therefore, a surgical needle can easily penetrate the vessel wall and the artificial vessel can be easily sutured with vital vessels. Moreover, even if the sutures are pulled, the sutures are not broken nor is the surgical string deviated Furthermore the holes formed by the needle close by themselves when the needle is removed because the vessel wall is made of the elastomer, thus avoiding leakage of blood. In addition, the artificial vessel of this invention does not form kinks when blood pressure is exerted on the vessel wall. It is considered surprising that the compliance of the artificial vessel of the present invention is approximate to that of a vital vessel.

The artificial vessel and the process of the present invention have the following characteristics.

(1) The compliance of the artificial vessel is approximate to that of a vital vessel.
(2) The artificial vessel has the desired porosity, as occasion demands.
(3) The artificial vessel has the following essential properties for a grafting vessel.

The surface in contact with blood has a superior blood compatibility.

A surgical needle easily penetrates the vessel, and thus the vessel is easily sutured.

There is no fraying at the cut ends when a vessel is cut to a desired length.

A surgical string cannot be deviated at the suture.

A throughout bore formed by a needle can close by itself.

Kinks are not formed when blood pressure is applied.

(4) The artificial vessel which has the above properties (1), (2), (3) can be prepared from the elastomer solution easily, homogeneously and inexpensively.
(5) The size of the artificial vessel can be easily adjusted by changing the size of the annular nozzle.

Therefore, the artificial vessel of the invention can be used as an artificial vessel, an artificial vessel for a by-pass, a material for a patch in vascular reconstruction surgery of a vital vessel, moreover, a blood access. In addition, the artificial vessel with a compliance of 0.1 to 0.8 can be used as an artificial artery. Since the artificial vessel of the present invention has a compliance approximate to that of a vital vessel, good blood compatibility and a desired diameter, the artificial vessel can be used as an artificial artery of a small diameter of 1 to 6 mm and a compliance of 0.1 to 0.5 which artificial vessel has not hitherto been available in clinical use. Such artificial vessel is preferably used in vascular reconstruction surgery of arteries below the knees and as a by-pass between the aorta and coronary. In addition, the artificial vessel of the present invention can be used as an artificial vein by covering the outside of the vessel wall with a net having a small compliance, and as a substituent for a flexible vital vessel such as a ureter.

The present invention is more particularly described and explained by means of the following Examples. It is to be understood that the present invention is not limited to the Examples and various changes and modifications may be made in the invention without departing from the spirit and scope thereof.

EXAMPLE 1

In 80 ml of N,N-dimethylacetamide was dissolved 20 g of polyurethane which is disclosed in Example 1 of Japanese Unexamined patent publication (KOKAI) No. 188458/1983. After defoaming the solution sufficiently under reduced pressure, the solution was extruded from the annular nozzle having an inner diameter of 3 mm and an outer diameter of 4.5 mm, with a gear pump at a constant rate of 40 cm/min. At the same time, water was injected into the inside of the tubular material at the same rate as the extrusion rate of the solution. The extruded tubular solution was immediately immersed into water to precipitate the elastomer tubularly. After removing the solvent by washing with water, the elastomer was cut to a desired length to give an artificial vessel.

The inner and the outer diameters of the artificial vessel obtained were about 3 mm and about 4.5 mm, respectively.

The section of the artificial vessel wall was observed with a scanning type electron microscope. A sketch of the photograph and a magnified view thereof are shown in FIGS. 2 and 3, respectively.

When the artificial vessel was cut and the cut end was sutured with a vital vessel at a distance of 1 mm from the end, the penetration of a surgical needle was similar to that in a vital vessel, and the cut end was never frayed. Further, the vessel was not broken even when the suture was pulled. In addition, the bores formed by the surgical needle closed by themselves when the needle was removed.

After being cut to 8 cm, the artificial vessel was inserted into a closed circuit. ACD blood of bovine origin was fed into the closed circuit by a quantitative pump which fed 0.05 ml per stroke, and the change of the inner pressure was measured. The compliance calculated according to the equation (I) on the basis of the number of strokes and the change of the inner pressure was 0.35. Furthermore, when the artificial vessel was bent at an inner pressure of 50 to 150 mmHg, no kinks were formed.

As a result of the above data, it is clear that the artificial vessel has excellent properties as an artificial artery of small diameter.

EXAMPLE 2

A prepolymer was prepared from 2 moles of 4,4-diphenylmethane diisocyanate and 1 mole of polytetramethylene glycol having a molecular weight of 2000. The chain of the prepolymer was extended by using 1 mole of ethylenediamine to give a segmented polyurethaneurea. In a mixed solvent of 57.5 ml of N,N-dimethylacetamide and 25 ml of propylene glycol was dissolved 17.5 g of the segmented polyurethaneurea. After defoaming under reduced pressure, the solution was injected into an annular nozzle having an inner diameter of 3 mm and an outer diameter of 4.1 mm, with a gear pump at a constant rate, and then was extruded tubularly. At the same time, defoamed water was injected into the inside of the tubular material at a rate of 1.2 times the rate of extrusion of the solution. The extruded solution was immediately immersed into water to precipitate the elastomer tubularly. After removing the solvent by washing with water sufficiently, the elastomer was cut to a desired length to give an artificial vessel.

The inner and the outer diameters of the artificial vessel were about 3 mm and about 4.1 mm, respectively. The section of the vessel wall had a spongy structure. The compliance determined in the same manner as in Example 1 was 0.4.

The cut end of the artificial vessel was not frayed. Furthermore, the suture of the artificial vessel with a vital vessel was very easy, and the sutures were not frayed even if they were pulled, and also the bores formed by a surgical needle closed by themselves when the needle was removed.

EXAMPLE 3

To 80 ml of N,N-dimethylacetamide was added 20 g of casein powder having a particle size of 30 to 50 $\mu$m, and the casein powder was dispersed in a homogenizer. In the casein dispersion was dissolved 20 g of polyurethane which is disclosed in Example 1 of Japanese Unexamined Patent Publication (KOKAI) No. 188458/1983. After defoaming sufficiently under reduced pressure, the solution was extruded from the annular nozzle having an inner diameter of 3 mm and an outer diameter of 4.5 mm, with a gear pump at a rate of about 40 cm/min. At the same time, defoamed water was injected into the inside of the vessel at a rate of 1.2 times the extrusion rate of the elastomer solution. The extruded tubular solution was immediately immersed into water to precipitate the elastomer tubularly. After removing the solvent by washing with water sufficiently, the tubular elastomer was cut to a desired length. The tubular material was immersed into a sodium hydroxide solution of pH about 13 to elute the casein particles with stirring. After the casein was completely dissolved, the sodium hydroxide was removed by washing with water to give an artificial vessel.

The inner and the outer diameters of the artificial vessel were about 3 mm and about 4.5 mm, respectively. In the inner surface area and the outer surface area were skin layers having uniform pores of 20 to 30 $\mu$m in maximum diameter. The section of the vessel wall of the artificial vessel had a spongy structure and the partition wall which formed the spongy structure had similar pores. The skin layer and the partition wall had a large number of very small pores and holes of less than 1 μm, which were formed by replacement between the good solvent and the coagulating liquid, in addition to the pores of 20 to 30 μm in maximum diameter.

The artificial vessel was observed with a scanning type electron microscope. Sketches of a section of the vessel wall and a magnified view thereof are shown in FIGS. 4 and 5, respectively. The inner surface of the artificial vessel is shown in FIG. 6. The artificial vessel had a porosity of 83% by volume.

The cut end of the artificial vessel was not frayed. Furthermore, the suture of the artificial vessel with a vital vessel was very easy, and the sutures were not frayed even if the sutures were pulled, and also the bores of a surgical needle closed by themselves when the needle was removed.

The compliance of the artificial vessel containing the casein (determined in the same manner as in Example was 0.45. Furthermore when the artificial vessel was bent at an inner pressure of 50 to 150 mmHg, no kinks were formed.

As a result of the above data, it is clear that the artificial vessel has excellent properties as a artificial artery of small diameter.

What is claimed is:

1. An artificial vessel comprising a vessel wall made of a thermoplastic elastomer, wherein said vessel wall comprises
   (1) a skin layer which forms the inner surface of the vessel wall,
   (2) an outer surface, and
   (3) an interior region between said inner surface and said outer surface, said interior region having a spongy structure characterized by cells, each cell being a void space surrounded by partition walls, wherein said vessel wall is prepared from a solution of said thermoplastic elastomer in a good solvent for said thermoplastic elastomer, and said inner surface, outer surface, and partition walls contain:
   (a) small pores of less than 1 μm in diameter formed by replacement of said good solvent with a coagulating liquid for said thermoplastic elastomer in said coagulating liquid,
   (b) large pores of 1 to 50 μm in diameter which are in continuous communication with each other throughout the interior region of the vessel wall, thereby communicating the inner surface of the vessel wall to the outer surface of the vessel wall, said large pores being formed by elution of pore-forming particles contained in said solution of thermoplastic elastomer,
   wherein the porosity of the artificial vessel is 75 to 87.5% by volume, and the compliance of the artificial vessel is 0.1 to 0.8.

2. An artificial vessel as in claim 1, further comprising a skin layer which forms the outer surface of the vessel wall.

3. The artificial vessel of claim 2, wherein the inner diameter of the artificial vessel is 2 to 6 mm, the thickness of the vessel wall is 0.2 to 1.5 mm and the compliance is 0.2 to 0.5.

4. The artificial vessel of claim 2, wherein the inner diameter of the artificial vessel is 2 to 6 mm, the thickness of the vessel wall is 0.4 to 1.3 mm and the compliance is 0.3 to 0.5.

5. The artificial vessel of claim 1 wherein the inner diameter of the artificial vessel is 2 to 6 mm, the thickness of the vessel wall is 0.2 to 1.5 mm and the compliance is 0.2 to 0.5.

6. The artificial vessel of claim 1 wherein the inner diameter of the artificial vessel is 2 to 6 mm, the thickness of the vessel wall is 0.4 to 1.3 mm and the compliance is 0.3 to 0.5.

* * * * *